United States Patent [19]
Gorretta et al.

[11] Patent Number: 6,009,186
[45] Date of Patent: Dec. 28, 1999

[54] METHOD AND APPARATUS FOR HARVESTING CROP MATERIAL

[75] Inventors: Nathalie Gorretta, Villevieille; Jean-Louis Vigneau, Lunel; Dominique Clanet; Jean-François Bonicel, both of Montpellier; Jean-Paul M. L. Martin, Le Fenouiller; Daniel H. A. M. Le Nevé, Challans; Jean-Paul Berthet, La Chaize Giraud, all of France

[73] Assignee: New Holland Braud S.A., Coex, France

[21] Appl. No.: 08/932,015

[22] Filed: Sep. 17, 1997

[51] Int. Cl.[6] .............................. G06K 9/00; G06K 9/36; A01D 46/00; B07C 5/00
[52] U.S. Cl. .......................... 382/110; 382/286; 56/330; 209/577; 209/597
[58] Field of Search .................................... 382/110, 286; 348/89, 144; 56/330; 209/576, 577, 587, 597

[56] References Cited

U.S. PATENT DOCUMENTS

| | | | |
|---|---|---|---|
| 4,015,366 | 4/1977 | Hall, III | 382/110 |
| 4,227,211 | 10/1980 | Disbrow | 382/165 |
| 4,532,757 | 8/1985 | Tutle | 382/110 |
| 4,713,781 | 12/1987 | Brizgis et al. | 382/110 |
| 4,718,089 | 1/1988 | Hayashi et al. | 348/89 |
| 4,771,594 | 9/1988 | Deux et al. | 56/330 |
| 4,873,644 | 10/1989 | Fujii et al. | 56/10.2 |
| 5,253,302 | 10/1993 | Massen | 382/110 |
| 5,369,944 | 12/1994 | Robichaud | 56/330 |
| 5,440,127 | 8/1995 | Squyres | 250/341.8 |
| 5,450,716 | 9/1995 | Gidge | 56/330 |
| 5,642,610 | 7/1997 | Dupon et al. | 56/340.1 |
| 5,659,623 | 8/1997 | Conrad | 382/110 |
| 5,709,394 | 1/1998 | Martin et al. | 280/6.11 |
| 5,732,147 | 3/1998 | Tao | 382/110 |
| 5,764,819 | 6/1998 | Orr et al. | 382/110 |
| 5,848,185 | 12/1998 | Koga et al. | 382/173 |

FOREIGN PATENT DOCUMENTS 0226430 6/1987 European Pat. Off. .
6-261622 9/1994 Japan .

OTHER PUBLICATIONS

Digital Image Processing (Gregory A. Baxes, pp. 142–146), 1994.

Primary Examiner—Jon Chang
Assistant Examiner—Mehrdad Dastouri
Attorney, Agent, or Firm—Larry W. Miller; J. William Stader; Frank A. Seemar

[57] ABSTRACT

A method and apparatus for harvesting fruit determines the proportion of fruit in a mixture of products containing fruit and bodies foreign to the fruit by capturing at least one initial image of a surface of the mixture to be examined. The device then assigns to each image pixel of one of two extreme grey levels according to the initial grey level of the pixel relative to a set threshold and then records the number of pixels of at least one extreme grey level to determine a area ratio between areas occupied by fruit and foreign bodies in the image. The invention has particular application to the harvesting of fruit, berries and the like produced on trees or bushes grown in rows to use the calculated proportion of fruit to adapt at least one of the functioning parameters of the machine.

28 Claims, 10 Drawing Sheets

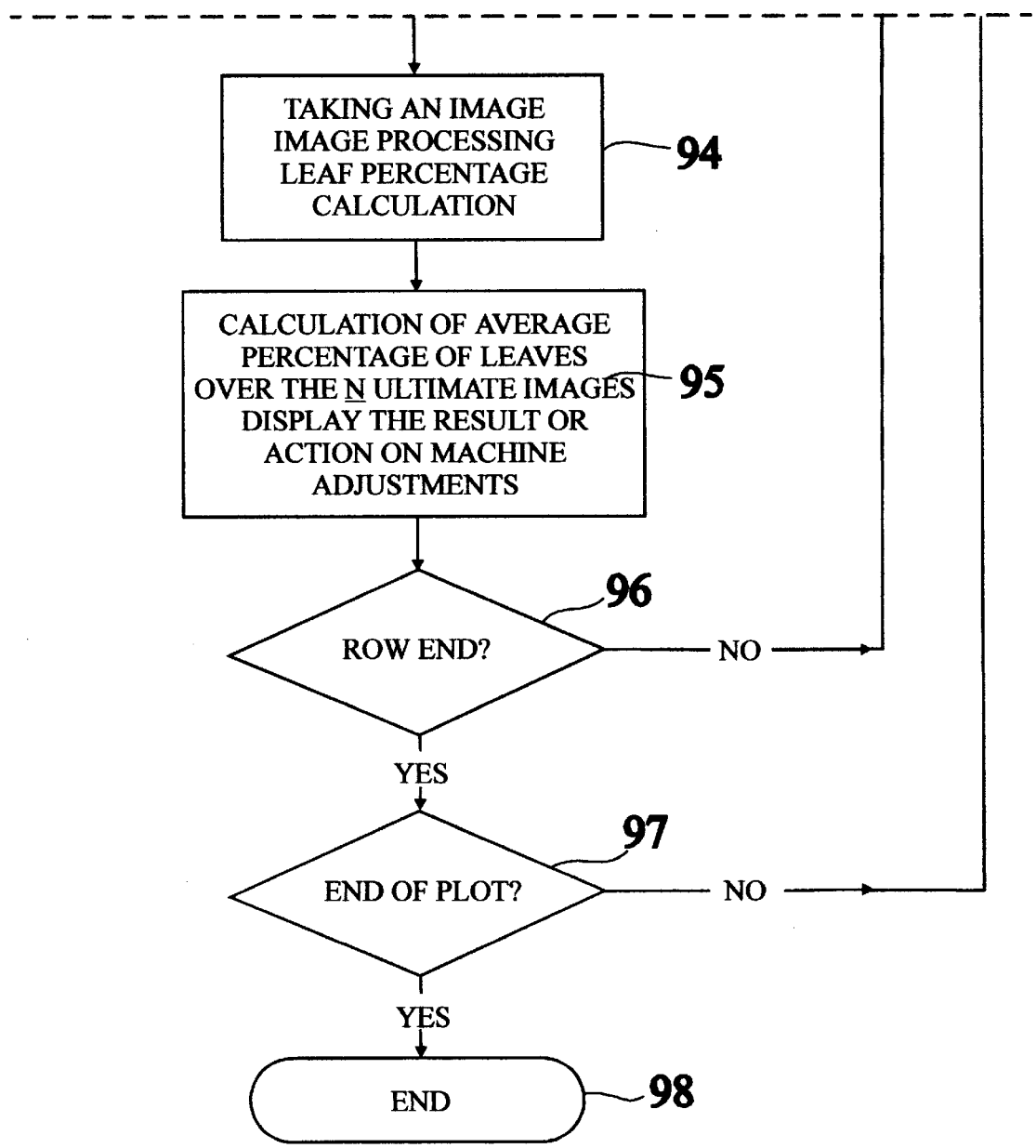

METHOD AND APPARATUS FOR HARVESTING CROP MATERIAL

BACKGROUND OF THE INVENTION

The present invention relates to a system for determining a proportion of foreign bodies in relation to fruit. The invention has particular application to the determination of a percentage of leaves and branches in a batch of fruit, berries and the like which have been harvested or of fruit, berries and the like grown on fruit trees or bushes. A particular application of this invention relates to the field of machines for harvesting fruit, berries and the like produced on fruit trees or bushes grown in rows. Such a machine comprises a high clearance chassis which can be travelled over fields and one or more shaker assemblies mounted on the chassis. The shaker assembly comprises one or more pairs of elongated shaker units which extend approximately horizontally in the direction of one of the longitudinal median axes of the machine.

The shaker units are spaced transversely to each other on either side of the longitudinal median axis. The shaker assembly also comprises a control mechanism connected to the shaker units to activate them in a synchronized reciprocating movement in a transverse direction in relation to the longitudinal median axis.

The invention will be described in relation to a particular example relating to the harvesting of grapes. However, it will be appreciated that the invention is also applicable to the harvesting of other fruits and berries, for example, black currants, gooseberries, raspberries and, more generally, to the harvesting of any fruit grown on trees or bushes planted in rows.

The principle of harvesting grapes is practically the same for most known grape harvesting machines. It involves shaking the vine by applying a sinusoidal, pseudosinusoidal or similar movement of the proper amplitude and frequency to detach the grapes or bunches of grapes. The movement is transmitted upon the vine by shaker units spaced so that they act either on the stock or vine or on the vegetation, that is, the fruiting area, depending on the type and number of shaker units used. The percentage of bunches and/or grape berries detached from the vine depends on the number and amplitude of the oscillations to which a given bunch of grapes is subjected. The more energetically and the more times a bunch is shaken, the more chance there is of said bunch or its individual grapes being detached from the vine. The number and amplitude of the oscillations to which a given bunch is subjected in turn depend essentially on various parameters which can be selected, particularly the amplitude and frequency of the control mechanism connected to the shaker units and the forward speed of the machine.

In detaching the bunches or grapes, the shaker units can also cause substantial detachment of leaves and/or breakage of shoots and/or buds. Apart from the fact that such damage compromises the future yield of the vine, the foreign bodies thus collected with the grapes cause problems with cleaning the crop which may lead to oenological problems.

The more energetically and the more times the shaker units act on the vine vegetation, the more and greater the above-mentioned damage will be. It is therefore normally necessary to find a compromise between the various above-mentioned parameters in order to obtain an acceptable percentage of harvested bunches or grapes without causing too much damage to the vine or complicating the cleaning of the crop.

Up to now, the working parameters of the harvester has been set manually by the driver based on visual observation of the harvest or of the vine plants after the machine has passed over them. Even though certain parameters such as shaker frequency can be adjusted from the driver's seat, such a visual check presents several inconveniences. Firstly, this inspection of plants and vines or of the crop is imprecise and depends on the driver's experience and powers of observation. Secondly, an unacceptable proportion of unharvested grapes on the vines or of foreign bodies (leaves, stems, buds) in the harvested crop can only be detected at the end of a row. The driver cannot inspect the contents of the temporary crop storage bin whilst the machine is travelling. Moreover, he cannot see the plants which have already been harvested because they are hidden behind the machine. Furthermore, the driver has to concentrate on driving the harvester both to align with the rows of vines and to control the speed of the machine on which, among other things, the number of times the shaker units act on a vine plant depends. It therefore would be very useful to have a system which might show the driver automatically what proportion of foreign bodies there was in the grapes harvested and/or the proportion of unharvested grapes after the machine had passed.

There are some optical systems for locating fruit on trees to enable a robot to pick it.

Document FR-A-2 658 624 describes such a system in which a camera provided with photosensitive charge coupled device (CCD) elements is used to find the coordinates of a fruit in a vertical plane parallel to the row of trees from which the fruit is to be picked. A robotized picking arm is directed at substantially right angles to the vertical plane towards the point of the fruit coordinate and the arm is slowed down near to the fruit by the action of an ultrasonic detector. The image processing means comprise means for activating a flash synchronously with the camera's integration periods.

Document EP-A-0-267 860 describes another system using several multi-color cameras to detect fruit on a tree and indicate successively to a robot with a picking arm the respective positions of fruit which it detects.

Document JP-A-6 261 622 describes a similar harvesting system which uses at least two infrared wavelengths.

Such systems do not provide a solution to the problems of examining the quality of the crop and the durability of the vine which the present invention aims to resolve. Moreover, in the above systems the processing of images is especially complex because it is necessary to detect the shape and coordinates of the fruit to be picked. Detection of shape serves, in particular, to distinguish fruit from foliage if their respective colors are similar.

There are also other crop sorting systems which use a camera working in the infrared field. For example, document FR-A-2 697 450 describes a system of sorting constantly moving fruit and vegetables to separate them from others, these being made up of non-fleshy parts. This system uses infrared rays in order to detect, by means of the difference in reflectivity between the fleshy and non-fleshy parts, the presence of a non-fleshy part in or attached to the fruit.

SUMMARY OF THE INVENTION

It is an object of the present invention to allow automatic real-time determination of the proportion of foreign bodies in the crop and/or of the proportion of unpicked grapes in the harvested vine plants.

More generally this invention aims to determine the proportion of bodies foreign to fruit in a batch of harvested fruit or the proportion of fruit on trees or bushes.

According to one aspect of the present invention, there is provided a method for harvesting agricultural crop material by means of a machine including the steps of determining a proportion of at least one product in a mixture of products containing crop material and bodies foreign to the crop material; and using the determined proportion to adapt at least one operating parameter of the machine which has an effect on said proportion.

The method may be a method to determine a proportion of one or more products in a mixture of products containing crop material and bodies foreign to the crop, comprising a near infrared shot taking step to obtain one or more initial images of an area of the mixture to be examined, a thresholding step consisting of allocating to each pixel of the image one of the two extreme grey levels dependent on the initial grey level of the pixel relative to a set threshold and a calculating step for the above proportion comprising the recording over one or more zones of the image resulting from the thresholding step of the number of pixels of at least one extreme grey level to determine an area ratio between the areas occupied respectively by crop material and the foreign bodies in the image.

When harvesting fruit, use can be made of the fact that leaves, vine stems and stock have reflectivities in near infrared which are very different from those of grapes, independently of their color, which allows a simple and precise determination of the proportion of foreign bodies to fruit or the proportion of fruit in relation to the mixture of products.

According to one embodiment of this invention, the threshold is derived automatically from the distribution of the grey levels in the initial image. The threshold is thus automatically adapted according to the actual average grey level of the fruit and the foreign bodies in the image. This makes the determination less susceptible to variations in intensity of the infrared rays, for example after a change in lighting.

The thresholding carried out on images helps to facilitate the determination of the proportion, by means of a single count of pixels with the same grey level. Furthermore, this thresholding makes it possible to implement further steps which improve the precision of the proportion or rate calculated.

According to an embodiment of this invention, the method also comprises carrying out, between the thresholding and recording step, one or more steps of erosion and dilatation of the image which was produced by the thresholding step. This step consists of determining the contours of the patterns which appear on the image from the thresholding with an initial extreme grey level corresponding to foreign bodies, of obtaining an intermediate image reducing the area of these patterns in a peripheral and regular manner by assigning the second extreme grey level to the pixels involved and of reconstituting an image to be subjected to the recording step by increasing the area of the patterns of the first grey level of the intermediate image in a peripheral and regular manner, the peripheral increment being made on a same number of pixels as the peripheral reduction carried out to obtain the intermediate image.

One advantage of such a step is that it enables the elimination of specular reflections on the grapes which on the images are translated by points of the same intensity as the leaves and stems. Such specular reflections are produced especially if the area under examination is brightly lit, for example, by means of flash.

According to an embodiment of this invention, the abovementioned proportion is determined by an average of area ratios determined from a series of images. So, although the images are interpreted two-dimensionally, it is possible to estimate the proportion of foreign bodies in a volume being progressively discharged within camera range. In the case of determining the proportion of fruit on trees or bushes, this determination can be made independently of the surface examined at each exposure.

According to another aspect of the present invention there is provided an agricultural harvesting machine including a chassis for travelling across fields; a harvesting assembly mounted on said chassis for harvesting crop material from the field; at least one conveyor for gathering the harvested crop material and guiding it into a temporary storage bin; and at least one device for determining the proportion of at least one product in a mixture of products comprising crop material and bodies foreign to the crop material.

Advantageously, the device comprises a means for taking infrared shots of an area of the said mixture of products under examination and a suitable means of image processing to determine a ratio of surfaces of fruit and foreign bodies over one or more zones of an image obtained by the camera, this processing means comprising means for carrying out the determination process described above.

According to an embodiment of this invention, the area under examination is lit artificially by a light source emitting at least within the near infrared range in order to minimize the effects of daylight. This artificial lighting is obtained preferably from a flash synchronized with a short exposure of the shot taking means. The shot taking means preferably consists of a camera equipped with photosensitive, charge coupled device (CCD) components associated with an electronic shutter means which determines very short exposure times of the photosensitive components.

According to an embodiment of this invention, the image subjected to the thresholding step is reconstituted by the difference between two frames of the same image or between two consecutive images which are taken respectively while artificially lighting the zone to be examined at least in the near infrared and, subsequently, without artificially lighting the zone to be examined. Such a method enables the elimination of infrared rays generated by the daylight. Only those rays generated by the artificial lighting source are taken into account when determining said ratio.

According to an embodiment of this invention which applies more particularly to the determination of the proportion of fruit on trees or bushes, artificial lighting is created during the image acquiring step from the back of the examined zone as seen from the shot taking means. The advantage of this method is that determination is thus not distorted by gaps in the foliage which could be interpreted as fruit.

In order to guarantee clear images, whether taken in temporary crop storage bins which are steadily filled or on trees or bushes, the camera preferably is provided with a fixed focal length lens and with an automatic definition sharpening device. The camera may, alternatively or additionally, be fitted with a motorized zoom lens.

One advantage of the present invention, when used for automatic adjustment of operating parameters of the machine, is that the driver of the machine now can concentrate on driving. The interpretation of the results of the determination of the foreign body ratio is carried out automatically and the parameters of the machine which have an influence on this proportion and therefore on the quality of the crop or the durability of the trees or bushes are, at least for some of them, automatically adjusted to these results.

Moreover, the corrections made to the machine's operating parameters are henceforth far more precise.

The operating parameters governed by the proportion of foreign bodies in the crop or of unharvested fruit are preferably selected from the following:

the frequency and/or amplitude of movement of the shaker units which constitute the shaker assembly mounted on a chassis of the machine to detach fruit, berries and the like from trees or bushes;

the forward speed of the machine in relation to the trees or bushes;

the linear speed of an intermediate conveyor for catching the detached fruit and conveying it to one or more temporary storage bins on the machine; and the parallelism of an approximately vertical median plane of the shaker assembly in relation to the trees or shrubs.

According to an embodiment of this invention, at least one determining device is associated to the temporary fruit crop storage bin for determining the proportion of foreign bodies in a batch of fruit collected in the bin. Besides the above-mentioned parameters, the air flow from at least one means for pneumatic cleaning of the crop tipped into said temporary storage bin may be controlled.

According to an embodiment of this invention, one or more determining devices are placed at the rear of the machine with respect to the direction of travel when harvesting to determine the proportion of fruit left on the trees or bushes.

This proportion of fruit can be determined directly or has the complement to 100% of the ratio of foreign bodies.

At least two determining devices in accordance with the invention are preferably associated with said temporary crop storage bin and with the rear of the machine respectively. In this way the operating parameters of the machine can be controlled while taking account of both the quality (cleanliness) of the crop and its yield. By achieving control by means of a control system which takes into account the two ratios (debris in the crop and unharvested grapes), these two proportions can be optimized by varying the machine's working parameters, without achieving optimization of one proportion at the cost of the other. For example, a more aggressive shaking of the vine could be envisaged in order to guarantee that all the fruit on the vine is harvested, but this action would result in the presence of more debris (foreign bodies) in the batch of harvested grapes. The combination of the two above-mentioned ratios would allow the machine to be adjusted so as to obtain a good proportion of grapes harvested and a good crop quality.

One advantage of this invention is that it thus enables the improvement of the yield of the current crop as well as of future crops, by optimizing the necessary compromise between shaking the trees or bushes and preserving their foliage.

BRIEF DESCRIPTION OF THE DRAWINGS

These objects, characteristics and advantages, among others, of this invention will be described in detail in the following description of specific embodiments, carried out in a non-restrictive way with reference to the attached figures, of which.

DETAILED DESCRIPTION OF THE PREFERRED EMBODIMENT

For reasons of clarity, the same elements have been given the same references in the different figures. For the same reasons, only those elements necessary for the understanding of the invention have been shown and will be described below.

Firstly, with reference to FIGS. 1 to 9, the method and the device establishing the proportion of foreign bodies to grapes or grapes to foreign bodies to be determined, in accordance with the first aspect of the invention, will be described.

Figure 1:
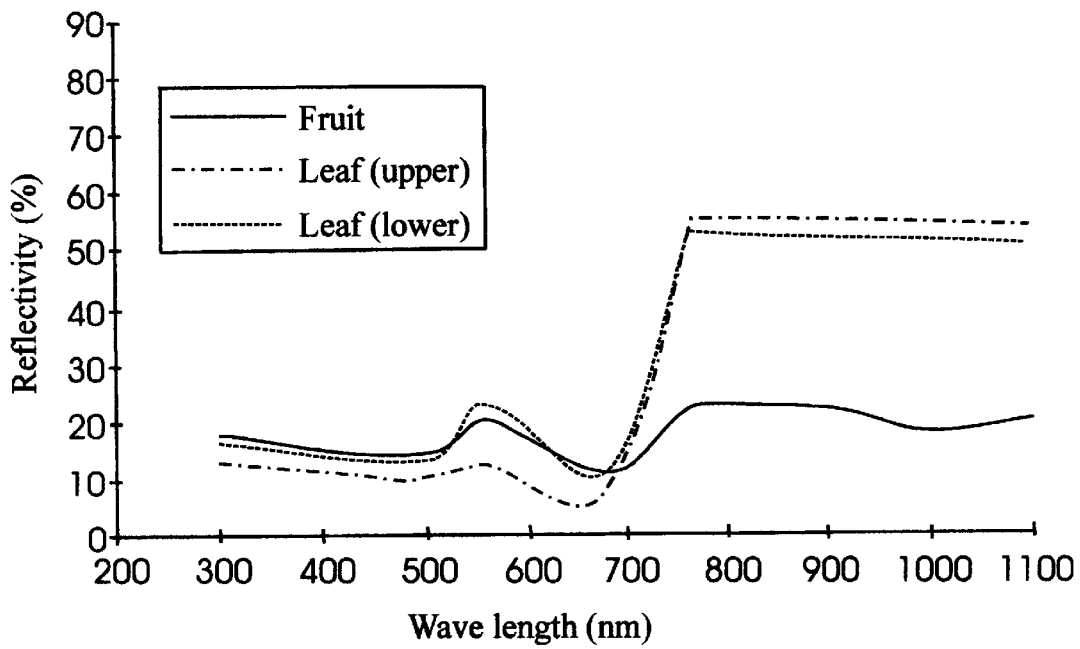
FIG. 1 represents, on the same diagram, the respective reflectivity of leaves and grapes as a function of their wavelength.

One aspect of the present invention is the use of the reflectivity of grapes in the near infrared range. This feature is illustrated in FIG. 1 which shows the reflectivity spectrum of the vine. In FIG. 1 are shown the respective spectra of the fruit (white grapes) and upper and lower surfaces (in the vine plane) of a leaf, the upper surface being quite glossy in appearance while the lower surface appears rather mat which shows up as a difference in reflectivity between the two surfaces. It can be seen that, although the difference in reflectivity between the leaf (especially on its lower surface) and the white grape is very small for wavelengths less than 700 nm (in the visible sphere) this difference in reflectivity is very clear in near infrared (wavelengths of over 800 nm).

This characteristic is due to the presence of sugar and water in fruit which have a larger rate of absorption of infrared rays and it expresses itself in a greater reflectivity of the leaves. Thus, although grapes, particularly white grapes, have approximately the same reflectivity as leaves, the reflectivity of the grape in near infrared is independent of color and has a markedly different value from that of leaves.

Moreover, the method can therefore be transposed to any fruit which contains more sugar and/or water than the foreign bodies irrespective of the color of the fruit and the foreign bodies.

Figure 2:
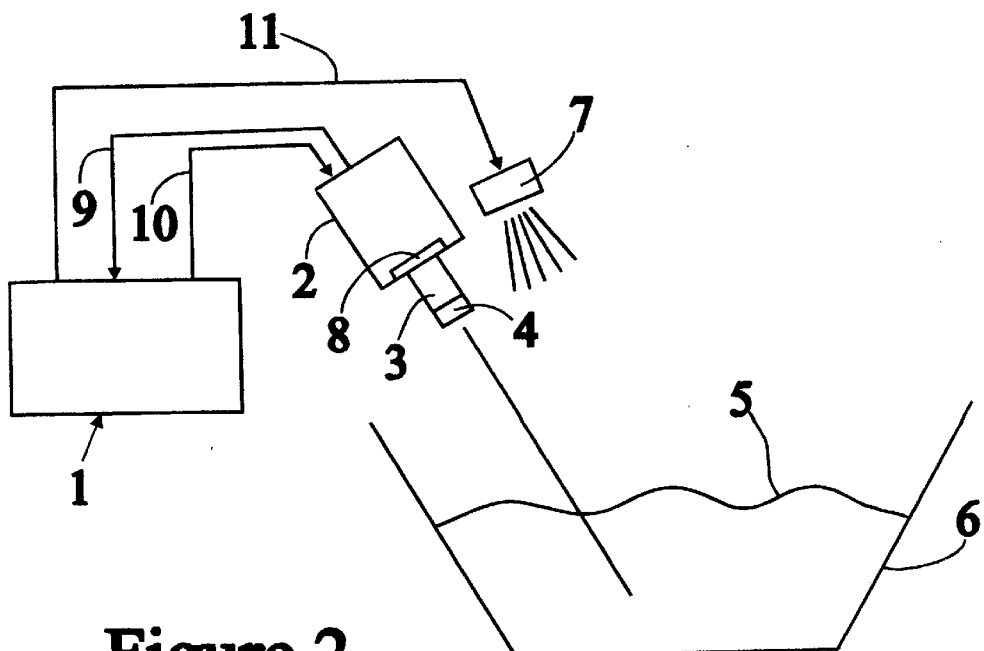
FIG. 2 is a schematic representation of a device for determining a proportion of bodies foreign to fruit in a mixture of fruit and foreign bodies according to one embodiment of the present invention.

FIG. 2 is a schematic representation of a device for determining a percentage of leaves and vine limbs for example in a batch of harvested grapes.

Figure 3:
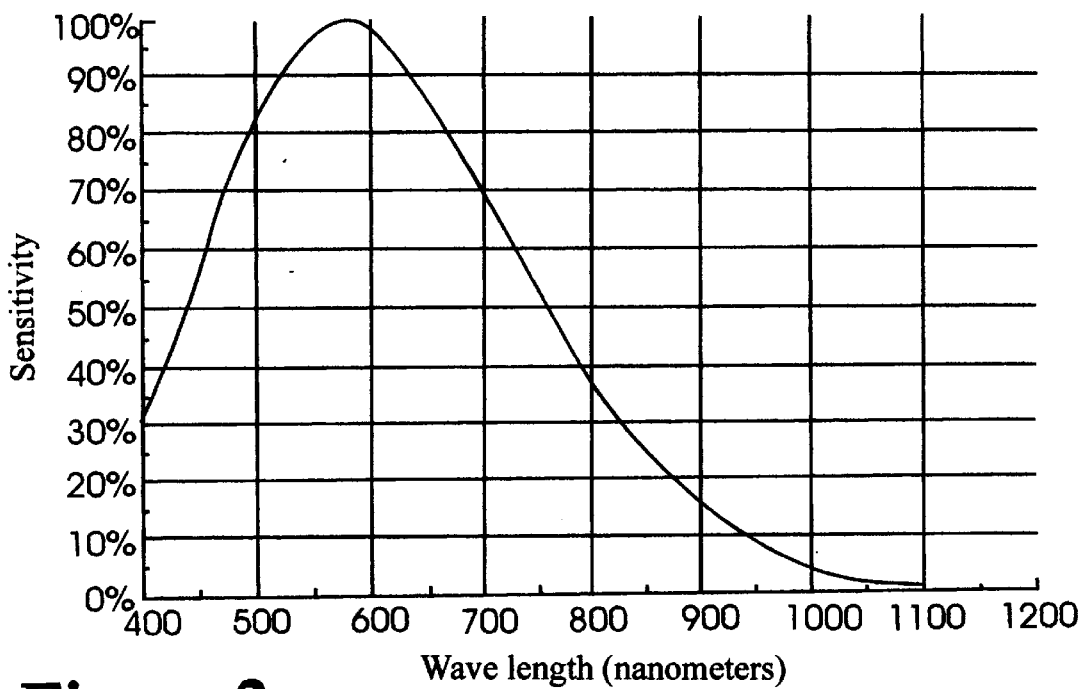
FIG. 3 represents the spectral response of a camera of the device shown in FIG. 2.
Figure 4:
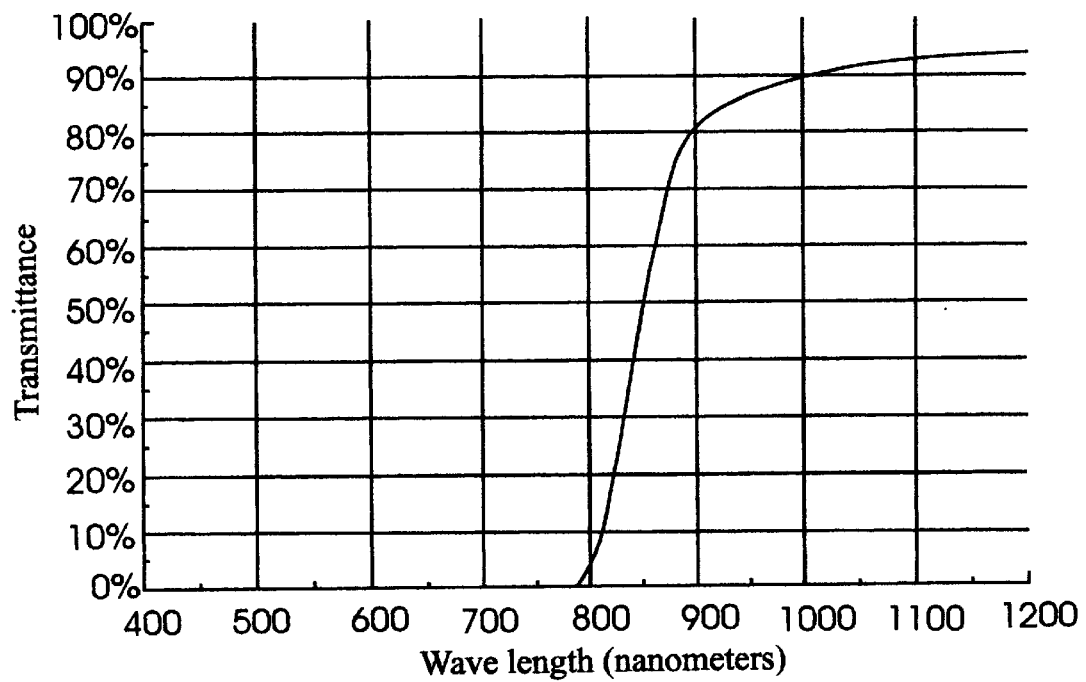
FIG. 4 represents the transmittance of an optical filter associated with a camera of the device in FIG. 2.

This device comprises a system 1 for processing images from a camera 2 for monochrome pictures. Conventionally, the camera comprises a sensor device with charge coupled device (CCD) photosensitive elements. The camera 2 is chosen because its spectral response extends into near infrared. The spectral response of the camera 2 thus obtained is illustrated in FIG. 3. To the camera 2 (more precisely to its lens 3) is fitted a band-pass optical filter 4 with a transmittance graph in function of the wavelength as illustrated in FIG. 4. The role of the filter 4 is to eliminate all visible light and to transmit only the wavelengths within the infrared range (above 800 nm).

According to a first application of the invention, the camera 2 is directed towards a batch 5 of harvested grapes, for example towards the bottom of a temporary storage bin 6 attached to a grape harvester. In this application, two problems have to be overcome.

One problem is linked to the fact that the level of grapes in the bin 6 rises, so that the distance between the batch 5 and the camera 2 decreases as the bin 6 fills in the course of the harvest.

Therefore the lens 3 is, for instance, an automatic motorized zoom activated by a sensor sensing the grape level in the bin 6. The sharpness of the images is, for example, adjusted on the bottom of the bin 6 when it is empty. The zoom allows the area of the images examined to be kept constant whatever the level of grapes in the bin 6. Change of focus in the course of filling the bin does not necessarily mean that the sharpness has to be adjusted if the depth of field is sufficient. Alternatively, the lens 3 is fixed focus and the camera is associated to, if necessary, an automatic means (auto focus) for adjusting the focus to the distance between the lens 3 and the surface of the batch 5. In this case, the area of the images examined is not constant but this does not matter as the purpose is to determine a proportion or ratio and not an absolute quantity. Obviously, the camera may be associated to a motorized zoom lens and to an auto focus device at the same time.

A second problem is linked to the lighting of the batch 5. On the one hand, the continuous tipping of grapes and foreign bodies into the bin risks giving a blurred image if the exposure time is too long, consequent to insufficient lighting. On the other hand, the presence of uncontrolled ambient lighting (sun, shadows from the machine) risks distorting the measurements.

To guarantee image sharpness, one or more flash units 7 are attached to the camera 2. Thus, most of the lighting comes from the flash which lasts for only a short time (for example, less than one millisecond) and the movement of the grapes and foreign bodies in that time span is negligible. The camera 2 may also be fitted with a sensor with photosensitive components attached to some type of electronic shutter mechanism which, with a sufficiently short exposure time (integration period) produces the same result as the light from a flash.

In order to eliminate the disturbances following from ambient light, the bin 6 can be fitted with a hood or canvas sheet. Then continuous lighting or a flash is used. Nevertheless, the presence of a sheet over the bin complicates emptying the bin 6 when it is full and cleaning the same.

One preferred solution of the invention consists in providing both a flash unit 7 and a camera 2 fitted with photosensitive elements associated with an electronic shutter. In FIG. 2, the sensor with photosensitive elements associated with an electronic shutter mechanism is represented by a block 8. The exposure time is then kept very short (for example in the order of 100 microseconds) and light from the flash unit is synchronized with this exposure. In this way the influence of ambient light is reduced to a minimum. Alternatively, the flash is used for every other image or for every other frame of images. Then the effect of ambient light can be eliminated by comparing two consecutive images (or frames), the first image having a mix of ambient light and flash while the next image has only ambient light.

The camera 2 provides images in the form of a composite video signal supplied by a cable 9 to the processing system 1. The output rate of the images is, for example, 25 images/s. Anyhow, the processing system may not process all the images. The time lapse between two images processed by the system is, for example, between 0.5 and 10 seconds depending in particular on how frequently the proportion of foreign bodies needs to be calculated. Of course, in the case where the difference between two consecutive images from the camera is used to deal with the ambient light, this interval corresponds to the interval between two processed images, that is, between two groups of consecutive images. Operation of the camera 2 and flash unit 7 is synchronized by the processing system 1 by means of wired connections, 10 and 11 respectively.

Figure 5:
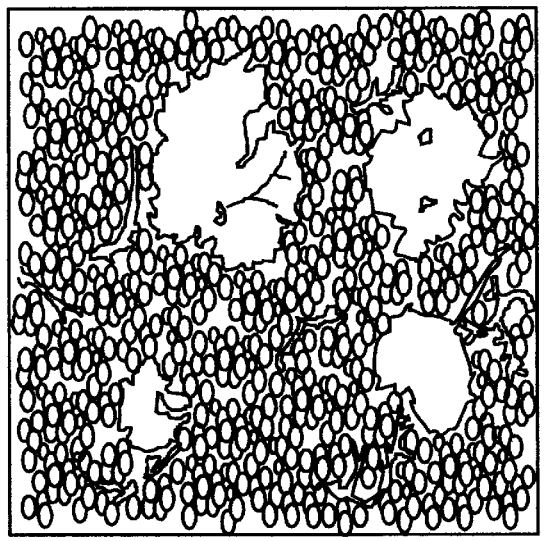
FIG. 5 is an infrared image of a batch of grapes and foreign bodies.

The purpose of the processing by the system 1 is to calculate the percentage of foreign bodies in relation to grapes in a batch of grapes and foreign bodies. FIG. 5 is a representation of an initial infrared image, i.e. an image relayed by the camera 2 fitted with the filter 4. The image includes both red and white grapes but they are not differentiated here for the reasons described above. On the other hand, the leaves and stalks stand out in clear contrast as a different "grey level". "Grey level" herein designates, by analogy with the analysis of a black and white image in normal visible range, the intensity of infrared rays captured on camera. The greater the infrared radiation coming from daylight or flash the higher the grey is said to be. By the same analogy, extreme levels (maximum and minimum) of infrared radiation captured by the camera will hereinafter be referred to, respectively, as "white level" and "black level".

The images are first digitized in a conventional way by the processing system.

Figure 6:
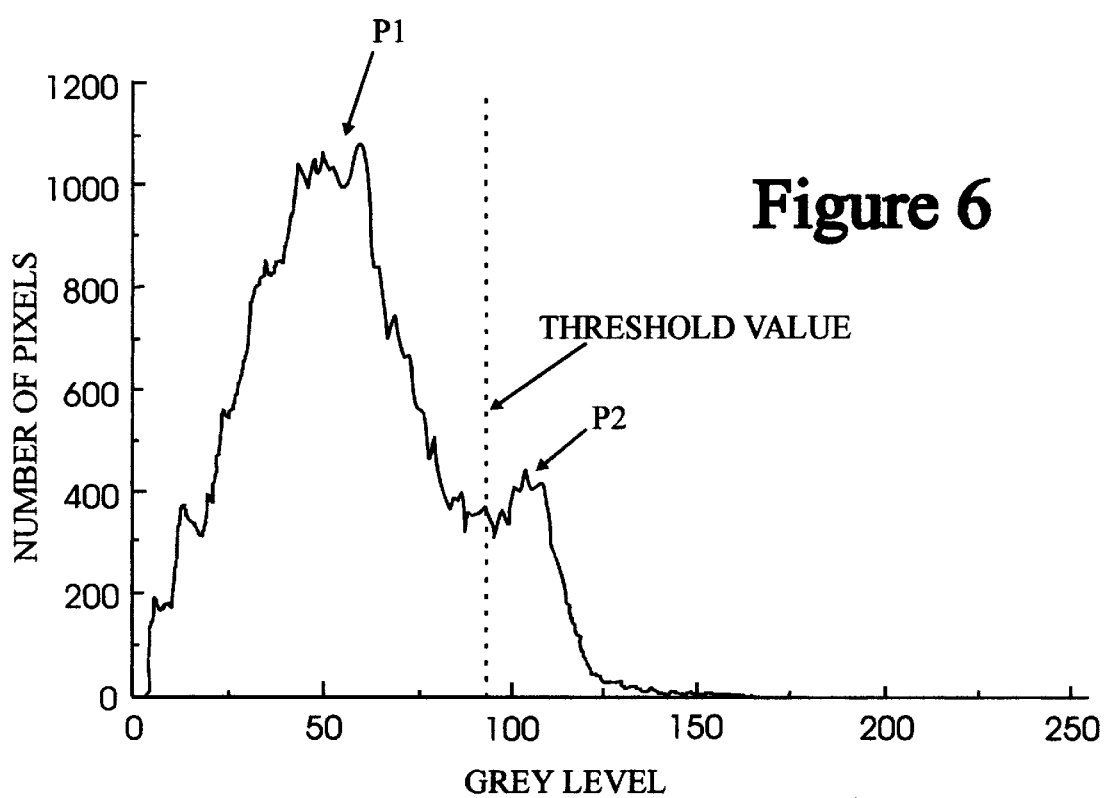
FIG. 6 represents a histogram of the grey levels of the image in FIG. 5.

In a first step of the method according to the invention an initial thresholding of the grey level image is carried out to increase the contrast between fruit and foreign bodies. The thresholding consists of detecting the grey level of each pixel of the initial image (between, for example, 0 for black and 255 for white) and allocating to it a new extreme grey level (0 or 255) according to whether its original grey level was above or below a certain threshold value. FIG. 6 is a histogram showing the number of pixels per grey level in the image reproduced in FIG. 5. An initial peak P1 corresponding to the darker pixels and a second peak P2 corresponding to the lighter pixels become apparent. The threshold indicated by a dotted line is between the two peaks P1 and P2. As will be seen below, the value of the threshold can be altered, in particular, in terms of the respective positions of peaks 1 and 2 in the grey scale. To all the pixels with a grey level less (less reflected radiation intensity) than the threshold level a black level will be attributed and to all the pixels with a grey level higher (higher sensed radiation intensity)

than the threshold a white level will be attributed. However, it will be appreciated that the choice of black and white is arbitrary. In fact, as all pixels are allocated a new extreme value, a new black or white level could likewise be allocated to all the pixels which initially had grey levels respectively higher or lower than the threshold value.

Preferably, the threshold is determined automatically by the processing system by analyzing the distribution of grey levels in the initial image. This automatic determination is made possible by recording the number of pixels for each grey level in the initial image in order to determine at what grey levels the two peaks P1 and P2 are located. Thus the trough between these two grey levels is determined by finding out what level, between the levels of peaks P1 and P2, corresponds to the least number of pixels. The threshold is fixed at this grey level. After thresholding, that is after allocation of one of the two extreme levels to each pixel of the initial image in accordance with the threshold so determined, an image is obtained such as that represented in FIG. 7.

It will be observed that it would be possible to determine, from the respective numbers of pixels on either side of the threshold value of the histogram in FIG. 4, an initial ratio indicative of the proportion of foreign bodies to fruit. However, this ratio may be considered to be too imprecise because of specular reflections present on the grapes and resulting from the lighting of the batch being processed, by the flash, the light from which included infrared radiation. This is why, according to a preferred embodiment, a second processing step is carried out called the opening-up or of the image patterns, the role of which is to eliminate specular reflections which are translated into points of high intensity and hence of high grey level of the image on FIG. 5. These points stand out better from the image in FIG. 7, which represents the same image as that in FIG. 5 at the end of the thresholding step and on which it can be clearly seen that the corresponding pixels have been made white.

The opening-up step consists of carrying out an erosion, then a dilatation of the outlines of the areas supposed to represent foreign bodies, here the white areas of the image. First the adjoining pixels of the same value are grouped together to determine the outlines of the white areas. Then, the image is eroded, that is, a black level is allocated to all pixels situated on the periphery of each white area. According to the size in pixels of the specular reflections this erosion is carried out on a relatively wide peripheral region of each white area. Thus, an intermediate image (not shown) is obtained in which all the small-sized white points, corresponding to specular reflections, have disappeared. In order to restore the original area to the other white areas (foreign bodies), a dilatation of the white areas of the intermediate image is carried out. This dilatation represents the inverse of an erosion, i.e. it consists of increasing the white surfaces by changing the levels of adjoining pixels outside the periphery of the white areas of the intermediate area from black to white. The opening-up step serves to "smooth out" the contours of leaves and make any small pieces of leaf disappear if necessary. Anyhow, this remains still negligible.

Figure 7:
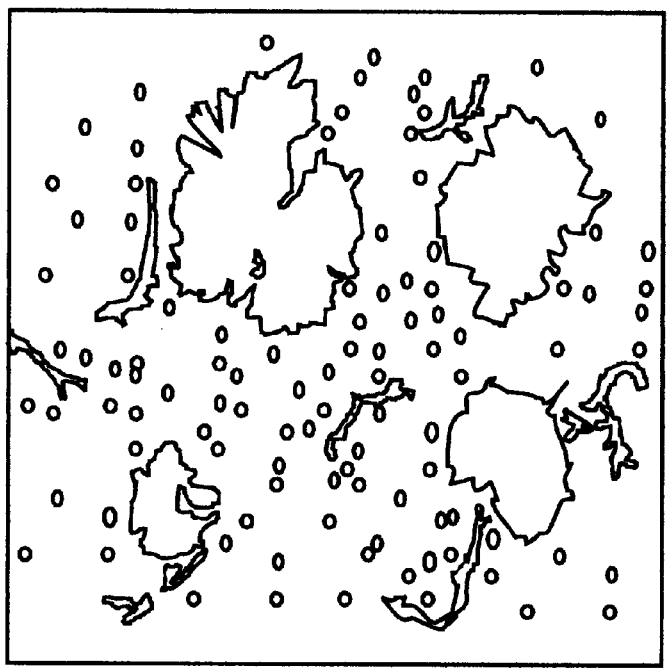
FIG. 7 represents the image in FIG. 5 after a thresholding step according to the invention.
Figure 8:
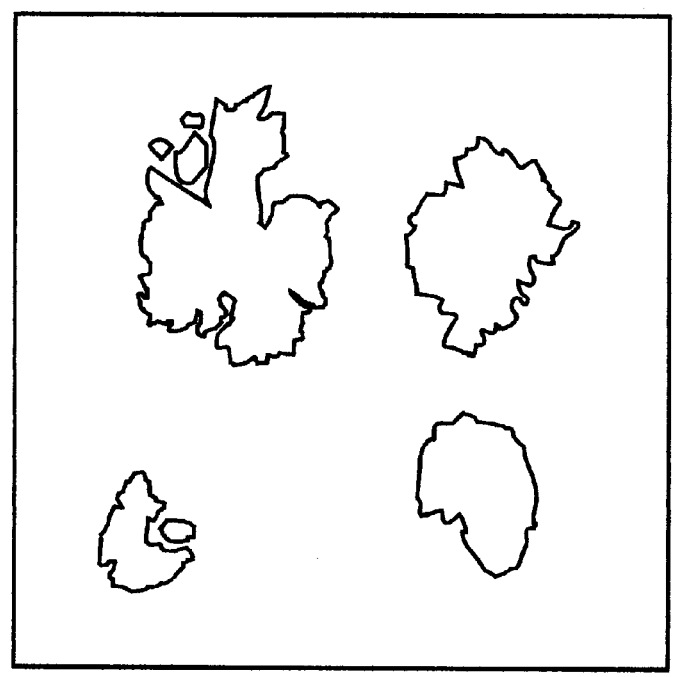
FIG. 8 represents an intermediate image after an erosion and dilatation step according to this invention.

A final image is then obtained represented in FIG. 8 in the case of the example taken in FIGS. 5 and 7. It can be seen that the stalks present in FIG. 7 have also disappeared. The erosion has, in fact, had the effect of eliminating the narrow areas. The elimination of the stalks by erosion constitutes an advantage for the precise determination of the proportion of foreign bodies which will be carried out subsequently, inasmuch as the stalks generally are not considered as foreign bodies in grape harvesting.

The proportion of foreign bodies to grapes is thus determined in a third step by recording the white pixels in relation to the black ones.

It may also be desirable to determine the proportion of vine limbs (not shown) in relation to leaves, i.e. the proportion of different constituents of foreign bodies to each other. To do this the white pixels are recorded after an initial erosion to eliminate the specular reflections, i.e. from the intermediate image above. A first number corresponding approximately to the total number of foreign bodies is obtained. Then a second erosion is carried out to eliminate the vine limbs, the white areas of which are narrower than those of leaves and have already been made narrower by the first erosion. The number of pixels made black on the periphery, that is, the size of the surrounding area eroded by the second erosion is a function of the width of vine limbs in the image. The white pixels are also recorded and a second number corresponding approximately to the leaves, is obtained. A third number of pixels is obtained corresponding approximately to the vine limbs by the difference between the two previous numbers. It will be observed that the number of pixels corresponding to the vine limbs and to the leaves can be added to the areas reconstituted by dilatation. In fact, by knowing the total number of pixels which correspond to foreign bodies in the final image (FIG. 8), it is possible to determine the ratio to be applied to the above third number to find out the proportion of vine limbs in the final image and therefore the proportion of leaves.

With slightly less precision it may also be acceptable to take the proportions of foreign bodies and vine limbs in the intermediate images without carrying out a dilatation. This has the advantage of eliminating the need to reconstitute the final image (FIG. 8) after a single erosion to determine the exact ratio of foreign bodies to grapes.

According to a second embodiment of the invention, the camera 2 is placed at the rear of the machine with respect to its normal direction of travel and is directed towards the trees or bushes planted in rows in order to determine the proportion or ratio of unharvested fruit, berries or the like, for example, the proportion of unharvested grapes. Apart from similar problems to those described with respect to the first application, here there is an extra problem to resolve. Indeed, the light intensity is inversely proportional to the square of the distance and therefore the background is hardly lit at all by the flash which lights the area to be examined. If the flash unit or units associated to the camera allow the next or preceding row of vines not to be apparent in situations where there is a gap in the foliage, this leads to any absence of foreground (gap in foliage, dead stock etc.) being translated into black on the image. However, in the infrared image, the bunches of grapes appear dark and the leaves light. After thresholding the bunches of grapes are therefore black. In this embodiment the purpose is to locate the bunches of grapes instead of the leaves and any lack of foreground will thus be recorded in the number of the bunches of grapes, which will obviously distort the measurement.

To solve this problem, a second flash unit or set of flash units or continuous lighting is installed opposite the camera in relation to the stocks for increasing the back-lit exposure. Thus the photosensitive elements corresponding to the gaps are highly stimulated and the gaps are interpreted as foreign bodies in relation to grapes. This is exactly what is desired in this application in which the device for determining the proportion of foreign bodies is, in fact, used to determine the proportion of bunches of grapes remaining on the vine.

Alternatively, opposite the camera in relation to the vine stocks a reflective background (for example a metal plate)

may be set up. However, this alternative arrangement is not a preferred embodiment because of the risk of the reflector becoming dirty which requires regular cleaning in order to preserve the accuracy of the determination of the unharvested fruit.

Figure 9:
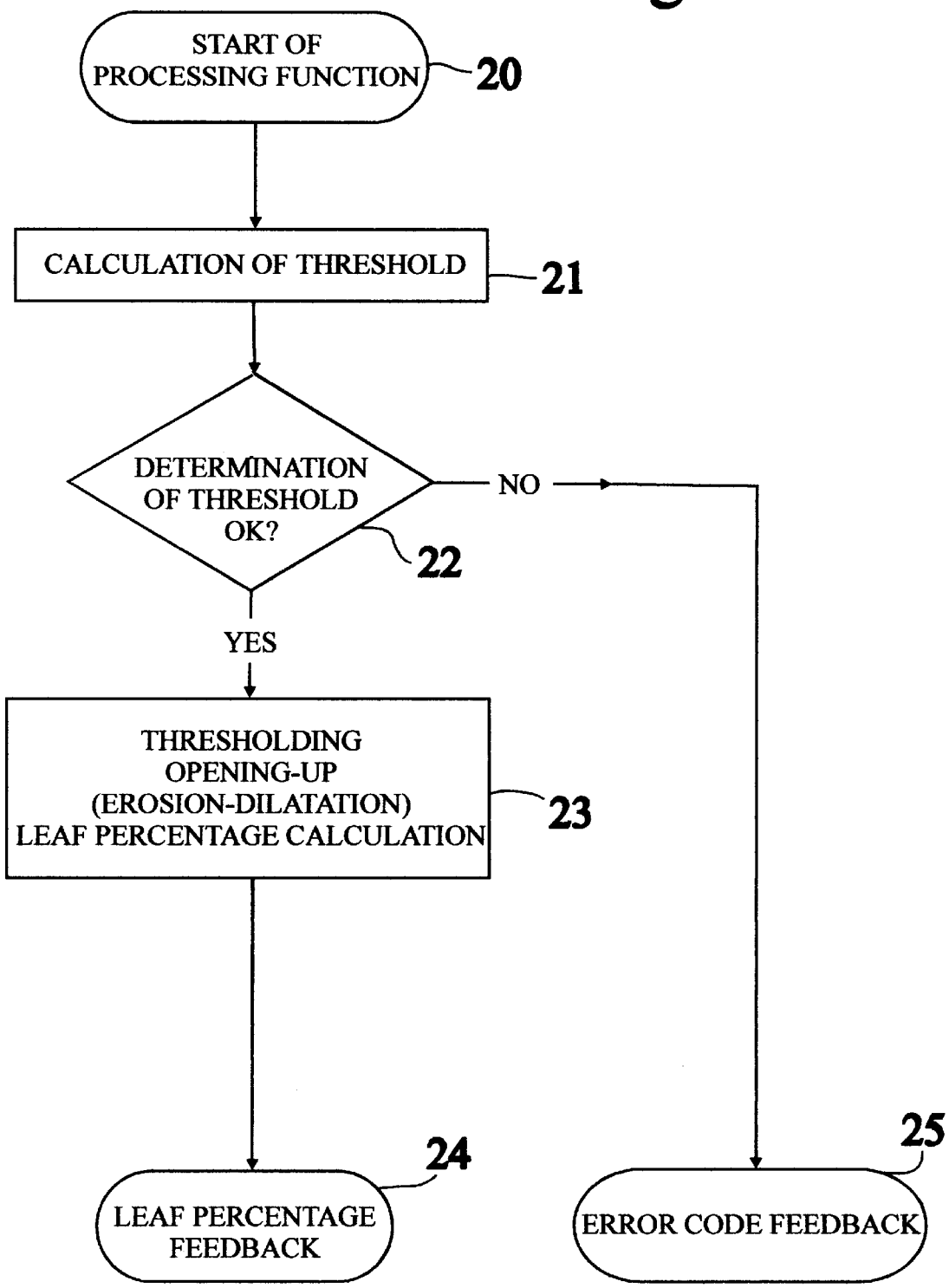
FIG. 9 represents a flow chart showing an embodiment of the image processing function according to the invention.

FIG. 9 shows the steps described above in the simplified form of a flow-chart according to a preferred method of processing the images applied to the determination of fruit, berries and the like in a harvested batch. When the data processing control program reaches the actual beginning (20) of the image processing function, the program starts by calculating (21) the threshold from the first image. Then it is verified (22) that it has been possible to determine a threshold. If this is the case, the thresholding, opening-up (erosion and dilatation) and calculating steps are implemented (23) and the function sends (24) the percentage calculated to the main program. Otherwise, the function (25) sends to the main program a code indicating a processing error. For application to the determination of proportion of fruit, berries or the like, the only difference is that steps 23 and 24 respectively, calculate a percentage of fruit.

Below is a description with reference to FIGS. 10 to 13 of a machine for harvesting fruit, berries and the like growing on trees or bushes planted in rows which is equipped with the means, according to the second aspect of this invention, for using the proportion of foreign bodies in relation to harvested fruit and/or the proportion of fruit left unharvested after the machine has passed in order to adapt one or more operating parameters of the machine which affect this or these proportions.

This second aspect will be described with reference to a specific example of a grape harvesting machine. However, it is observed that the invention applies equally to other types of machines for harvesting grapes or other fruit.

Figure 10:
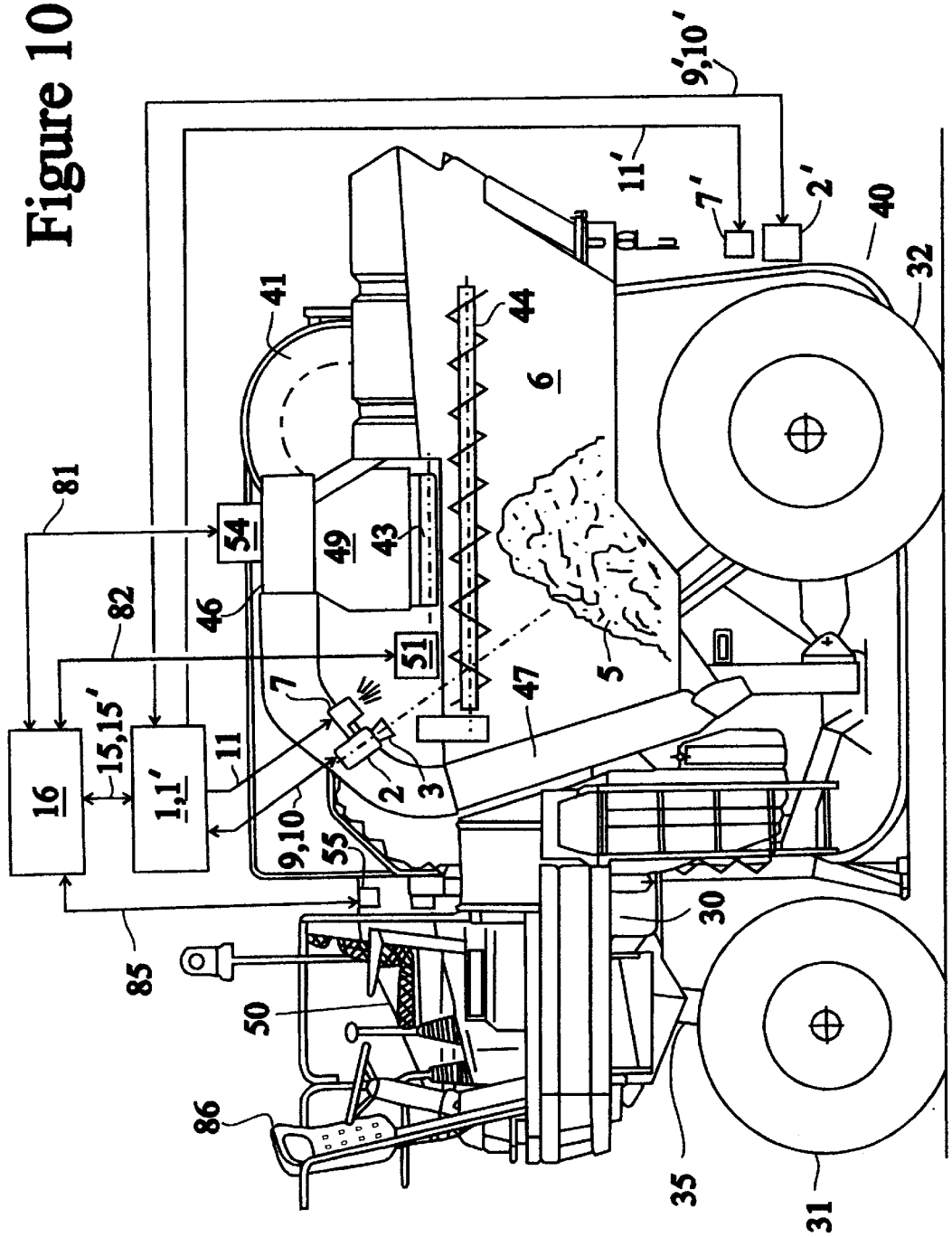
FIG. 10 represents a side view of a harvesting machine showing the positioning of devices for determining the respective ratios of foreign bodies in the harvested grapes and of unharvested grapes after passage of the machine according to an embodiment of the invention.
Figure 12:
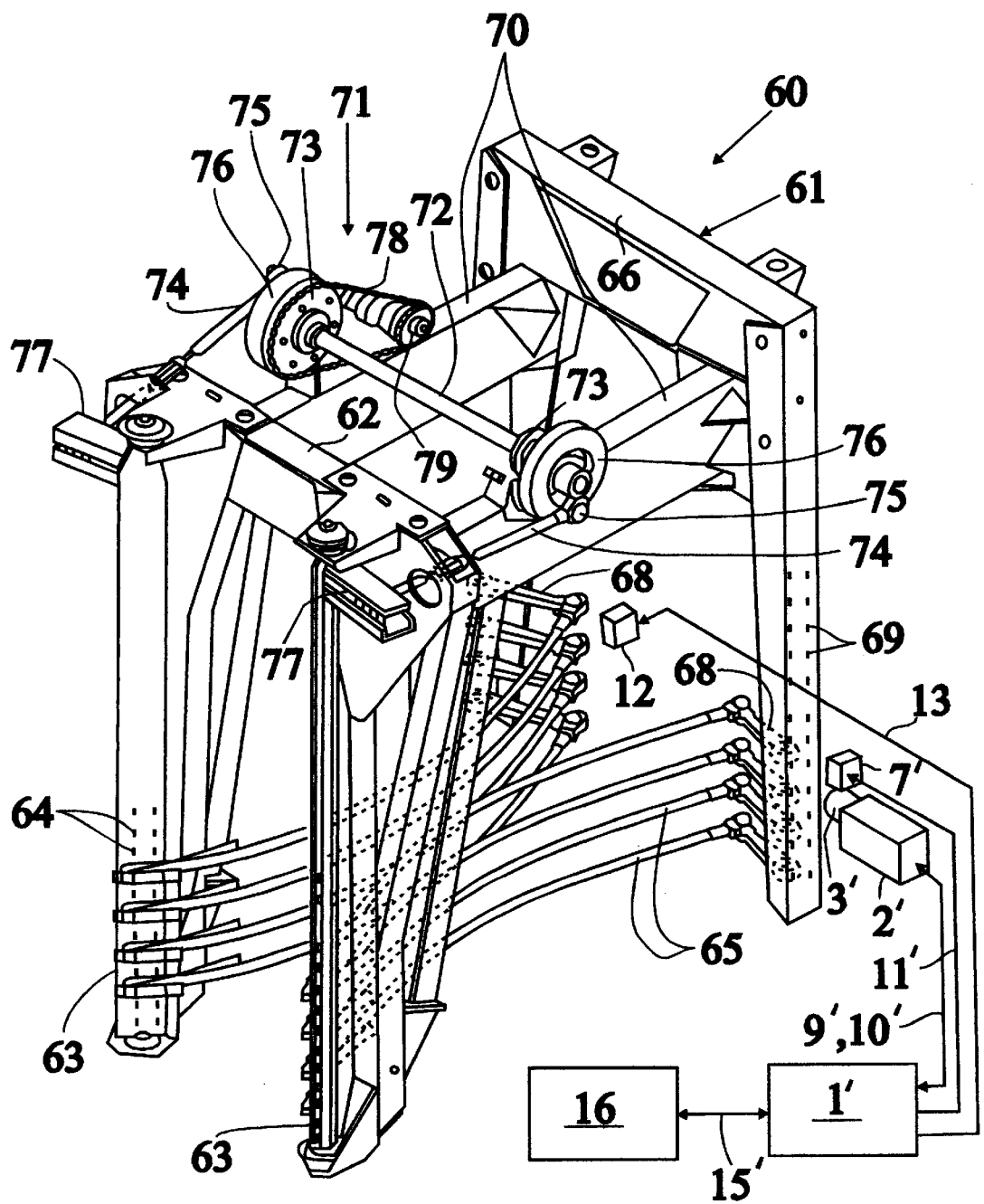
FIG. 12 represents an embodiment of a shaker unit for the machine shown in FIG. 10, showing the location of the device for determining the proportion of unharvested grapes after passage of the machine in accordance with an embodiment of this invention.

FIG. 10 is a schematic side view of a harvesting machine according to an embodiment of this invention. This machine comprises a conventional chassis 30 provided with front 31 and rear wheels 32 and having a boom shape to enable it to straddle a row of crops, in this case a row of vines. The chassis 30 supports a conventional harvesting assembly 40 comprising a shaker assembly 60 (FIG. 12).

Figure 11:
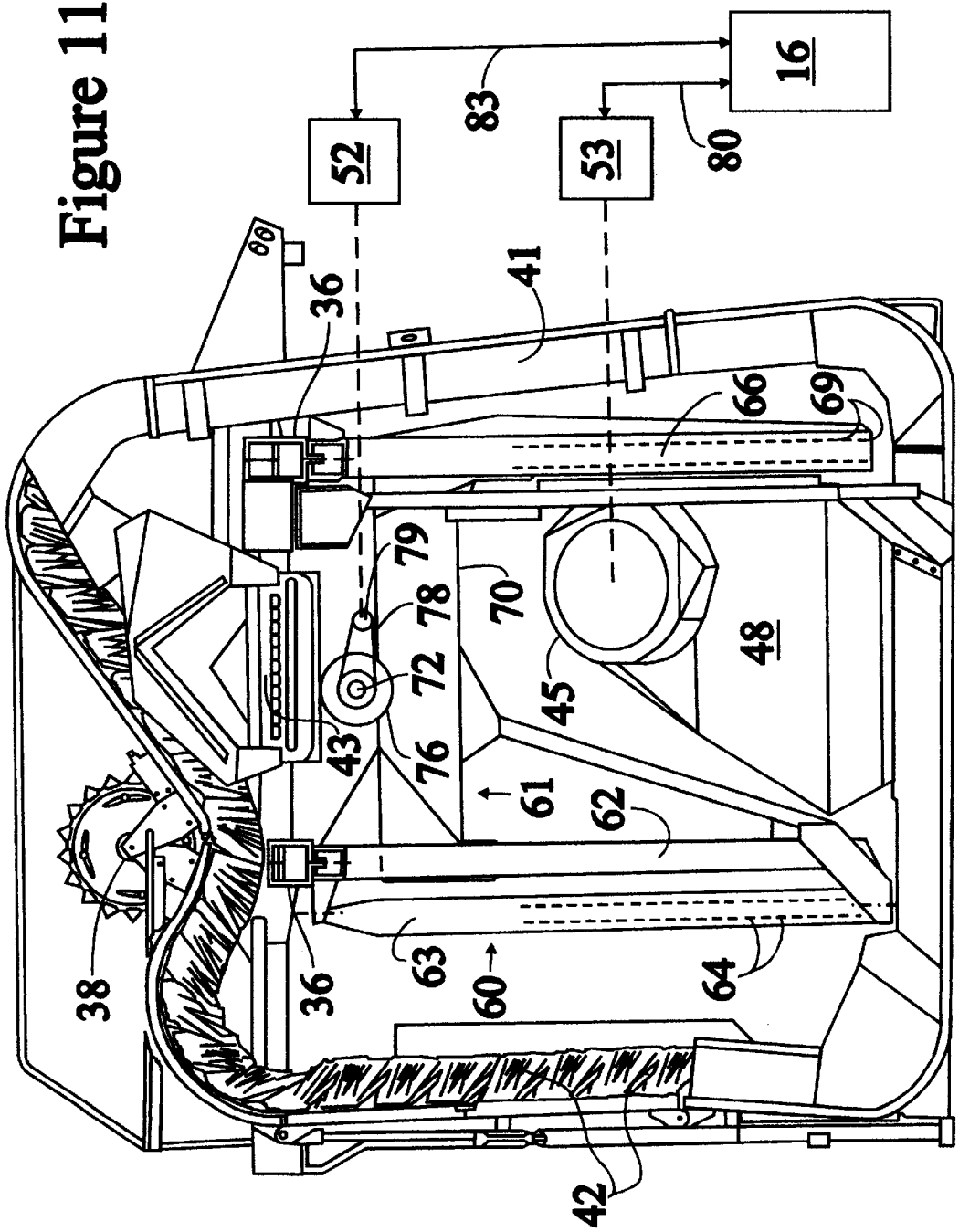
FIG. 11 represents in side elevation a part of the harvesting unit of the machine shown in FIG. 10.

The harvesting assembly comprises, in general, two identical portions positioned symmetrically in relation to a median vertical plane. FIG. 11 is a lateral elevation, showing a view taken along this plane and illustrating one of the two portions of the harvesting assembly 40 and FIG. 12 shows, in perspective, an example of a shaker assembly 60.

The harvesting assembly 40 can be permanently fitted to the chassis 30 or may take the form of an stationary assembly, which is mounted on the chassis 30 in such a way as to be removable for replacement with other equipment or accessories such as spraying, pruning, soil cultivation, etc. equipment.

In order to enable harvesting on sloping ground without de-stabilizing the machine, the wheels 31 and 32 are usually mounted on a telescopic tilt correction means 35. The tilt correction system helps to ensure that the vertical median plane of the shaker assembly remains parallel with the vine row.

Each portion (FIG. 11) of the harvesting assembly 40 comprises an elevator 41 constituted by a conveyor belt 42 with buckets (noria) to collect the grapes detached by the shaker assembly 60 and to convey them to an intermediate belt, for example, a conveyor apron 43 suitable to tip said grapes into a temporary storage bin 6 (usually two bins 6 are provided for either side of the machine, each being attached to one of the portions of the harvesting assembly 40).

The conveyor belts are driven by, for example, a system of gears driven by a shaft 38. The speed of the norias is equal to the forward speed of the machine and the driving sense is such that the buckets 42 are moved in the opposite sense to that of the machine in the area where they collect the grapes. Thus, the buckets 42 surround the vine stems without friction.

The function of the intermediate conveyor 43 is to guide the grapes, tipped out by the buckets 42, to an auger 44 (FIG. 10) for spreading the crop in the bin 6. The chassis 30 also supports a pneumatic crop cleaning means composed, for example, for each portion of the harvesting assembly 40, of a lower aspirator 45 associated with the respective conveyor 41 and an upper aspirator 46 associated with the respective bin 6 and the respective intermediate conveyor 43.

The function of the lower aspirator 45 is to eliminate part of the leaves which were detached from the vine limbs at the same time as the grapes, before these are collected by the buckets 42. The function of the upper aspirators 46 is to finish the crop cleaning by sucking out the remaining leaves when the crop is tipped into the bins 6 by the conveyor apron 43. The differences in weight and the coefficient of air penetration between the leaves and the grapes assist in the cleaning process. The aprons 43 ensure better spread of the crop in the areas where it falls into the bins 6 which also helps the cleaning process.

The leaves are discharged through suitable chutes 47 and ejected to the outside of the harvesting assembly 40. Each aspirator 45 or 46 is connected to a hood 48 or 49 respectively, directed, as the case may be, towards the area where the buckets receive the grapes detached by the shaker assembly 60 or towards the end of the apron 43 from where the crop is tipped into the bin 6. The aspirators may be replaced by blowers positioned in such a way that they blow the leaves out of the buckets 42 and/or out of the bin 6.

The shaker assembly 60 (FIG. 12) can be supported directly by the harvesting assembly 40 or by an auxiliary frame or chassis 61 carried on the chassis 30 or on the harvesting assembly 40. The frame 61 can be fitted in the usual way to the harvesting assembly 40 (or to the chassis 30) or be suspended from the top to adapt to the alignment of the row of vines. The frame 61 is, for instance, suspended from the harvesting assembly 40 or from the chassis 30 by means of shock-absorbing silent blocks 36. If the shaker assembly is suspended it may be linked to an electric or hydraulic system (not shown) for correcting the parallelism of the substantially vertical median plane of the shaker assembly to the vine row. In other words, if the tilt adjustment system is not able to ensure that the median plane of the shaker assembly merges with the vertical plane of the vine plant (for example, if the vine plants are leaning slightly from the vertical) the parallelism correction system enables the substantially vertical median plane of the shaker assembly to be aligned with the vine plants. If necessary, the harvesting assembly 40 may, alternatively or additionally, be mounted in a pendular manner to the chassis 30. In this case, it can also be connected to a similar parallelism correction system in order to assist in adjusting the parallelism of the shaker assembly with the vine plants.

The frame 61 comprises, at the front with respect the direction of movement of the machine, a front boom 62 for mounting two approximately vertical shaker plates 63 on bearings. These plates 63 have slots 64 for attachment of one end of the shaker rods 65 (not shown in FIG. 11) in accordance with to the vertical distribution of the crop in the vine row. The frame 61 also comprises a rear boom 66 to the pillars of which are attached, by means of short links 68, the other ends of the shaker rods 65. Individual articulation of the rods 65 by means of their respective links 68 allows the shakers to bend independently of each other. The links 68 are articulated individually on the boom 66 by means of appropriate brackets (not shown), the respective vertical positions of which are determined by slots 69 provided in the pillars of the boom 66.

Two side beams 70 interconnect the booms 62 and 66 at their upper ends. The beams 70 carry a drive mechanism 71 for oscillation of the plates 63 about the axes of their respective bearings. The mechanism 71 is, for instance, made up of two connecting rod and crank systems synchronized by a horizontal shaft 72 which is mounted for rotation in bearings 73 fitted on each respective beam 70. Two connecting rods 74 are each articulately connected at the one end, to an eccentric crankpin 75 on a flywheel 76 which is affixed to one end of the shaft 72 and, at the other end, to a substantially horizontal arm 77, linked to one of the shaker plates 63. The amplitude of the oscillations of the plates 63 is usually controlled by adjusting the position of the respective articulated connections of the rods 74 on the arms 77 in relation to the respective pivot axes of the plates 63. One of the flywheels 76 is rotated, for example, by a drive shaft 79 and chain 78 and its rotary movement is transmitted to the other flywheel 76 by the shaft 72. The respective crankpins 75 of the two flywheels 76 are diametrically opposed. The shaker rods 65 define an inlet convergent allowing the vegetation to be channelled gently towards the shaking area and an outlet divergent allowing the vegetation to be steadily released.

An engine 50 usually supplies the necessary power to the driving means of the various active components of the machine and to the wheel drive in the case of a self-propelled machine. Motive power to the wheels is usually provided by hydraulic motors which are supplied, by means of a hydraulic speed control system 55, by a fluid from a hydrostatic pump driven by the engine 50. Motive power to the conveyor aprons 43 and the drive shaft 79 of the shaker assembly 60, is e.g. provided by the hydraulic or electric systems, 51 and 52 respectively. The aspirators 45 and 46 are also usually powered by the hydraulic or electric systems, 53 and 54 respectively.

The harvesting machine described above is known in the art. For more details reference can be made to, for example, the description of documents FR-A-2 605 487 and FR-A-2 399 793, which are incorporated herein by reference.

According to the present invention, the harvesting machine is associated to one or more devices for determining a proportion of product in a mixture of products containing fruit and foreign bodies of the type described above with reference to FIGS. 1 to 9.

In the example illustrated in FIGS. 10 to 12 the machine comprises at least one first device for the determination of the proportion of leaves, vine stems and limbs in at least one bin 6 and at least one second device for the determination of the proportion of fruit unharvested after passage of the machine.

The first device comprises a system 1 (FIG. 10) for processing images provided by a camera 2, the lens 3 of which is directed to the bottom of the temporary storage bin 6. This camera is associated to one or more flash units 7. The second device comprises a camera 2' (FIGS. 10 and 12) installed at the rear of the machine. The lens 3' of the camera 2' is directed towards the median vertical plane to take shots of vine surfaces after harvesting. The camera 2' is associated to one or more flash units 7' for lighting the vine surfaces. One or more additional flash units 12' are situated in the median vertical plane opposite the camera 2' to create back lighting in the areas where there is no vegetation. The flash unit 12' is controlled via a wired connection 13' by an image processing system 1' connected to the flash unit 7' and the camera 2' by wires 11' and 9', 10' respectively.

The respective processing systems 1 and 1' for the images from the cameras 2 and 2' are depicted by blocks. Although this is not shown, these blocks are mounted on the chassis 30. Blocks 1 and 1' are connected, by suitable means 15 and 15' to a control system 16 of some machine components in accordance with the proportion or proportions determined. Eventually, blocks 1, 1' and 16 may be merged in a data processing system, for example, a central micro-computer unit mounted on the chassis 30.

The system 16 adjusts, in accordance with the proportion of leaves in the bin 6 determined by the system 1, the output from the aspirators 45 and 46 and/or the speed of the conveyor apron 43 and/or the oscillation frequency of the shaker plates 63, i.e. the rotation speed of the shaft 79, and/or the forward speed of the machine. The hydraulic or electric systems 53, 54, 51 and 52 respectively, which drive these units and the system 55 connected the engine 50, are, for this purpose, linked by wired connections 80, 81, 82, 83 and 85 to the system 16.

The proportion of unharvested grapes established by the system 1' serves in particular to adjust, by means of the system 16, the frequency of shaking and/or the forward speed of the machine.

The connections 80, 81, 82, 83 and 85 are two-way to allow the systems 53, 54, 51 and 52 and the speed regulator to supply data on the output of air from the aspirators, the speed of the conveyor belt 43, the frequency of oscillation of plates 63 and the forward speed of the machine. If necessary, separate sensors (not shown) are associated with the moving parts and communicate with the control system 16.

Other moving parts of the machine can, if required, be controlled by the established proportion or proportions. For example, the width of the shakers could be adjusted by making the positions of the articulations between the connecting rods 74 and the arms 77 remotely controllable by means of a suitable hydraulic or electric system. The system for correcting parallelism of the shaker assembly (and/or the harvester assembly) in relation to the vine plants could also be controlled, for example, by the proportion of unharvested grapes.

If required, two devices for determining the proportion of foreign bodies in the bins 6 and/or two devices for determining the proportion of unharvested grapes could be associated with each side of the machine. This helps to control the parallelism of the shaker assembly by enabling the assessment of an imbalance between the proportion of unharvested grapes on either side of the machine or between the proportion of foreign bodies in the bins attached to each side of the machine. If two devices are provided at the rear of the machine, then the extra flash unit 12 can be dispensed with, since the flash unit 7' on each device can be used as back lighting to the other device if they are correctly synchronized.

The system 16, preferably, also should be connected to a control console 86 with a screen and keyboard. The console 86 may be used, if necessary, to adjust, by means of the keyboard, the operation of the moving parts of the machine. This operator control is thus achieved in accordance with the proportion(s) determined by the units 1 and 1' and displayed on the screen of the console 86.

The practical implementation of the control system 16 is within the competence of the skilled person working from the teaching above. It would be possible, for example, to have recourse to a computer network connecting, by means of a computer bus, various electronic interfaces associated with to the operating systems of the moving parts of the machine, to a central data processing unit.

Figure 13A:
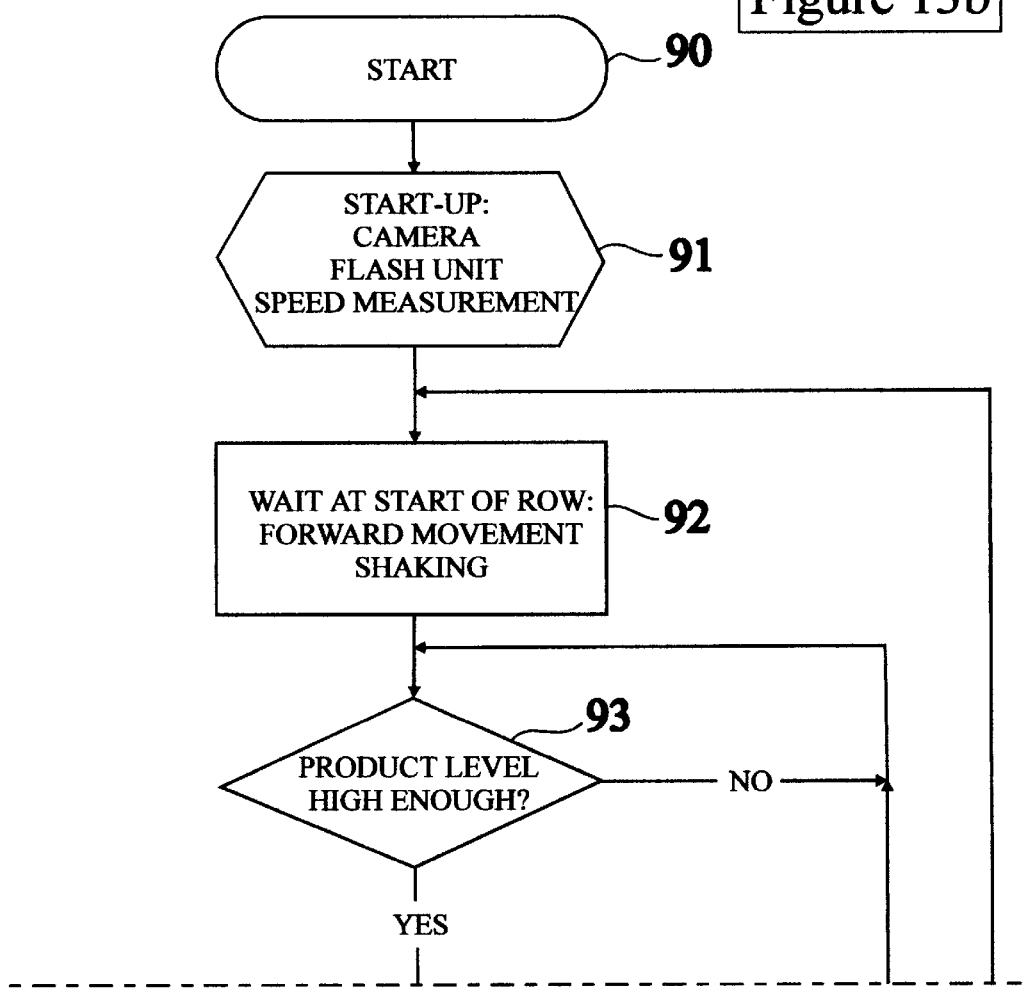
FIG. 13 represents a flow chart showing a method of implementing a system for controlling the moving parts of the machine according to the determination established by the device for determining the proportion of foreign bodies in the grapes harvested, shown in FIG. 10.

FIG. 13 shows, in the form of a flow chart, in simplified form, an embodiment of the harvesting method according to the invention. The flow chart in FIG. 13 shows how the system 16 works in relation to system 1, that is, with an examination of the batch 5 of fruit harvested in bin 6.

After starting up (90) the system 16, comes first the step of initialization (91) of the camera 2 and the flash unit 7 and of the means for measuring speeds (air flow, forward speed, frequency of oscillation) of the moving parts of the machine. Then there is a wait (92) for the start of a row of vines which is characterized by the forward movement of the machine and the starting up of the shaker assembly. The system then determines (93) whether the level of products in the bin is sufficiently high to begin determination of the proportion of foreign bodies. To do this, a sensor is used to detect the contents level, the sensor being associated in a known manner with the bin 6. Processing proper begins when the contents level reaches a predetermined threshold in order to avoid the inclusion of images of the bottom of the bin 6 which would distort the measurements (the bottom being interpreted as grapes). When the level threshold is reached, the system 16 commands (94) the system 1 to obtain an image, process the same and calculate a percentage of leaves and foreign bodies in accordance with the processing method described above (FIG. 9).

The step (94) is carried out several times at short intervals to allow the system 16 to calculate (95) the average percentage of leaves in n images for displaying the result or adjusting the moving parts of the machine. The interval between two images processed by the system 1 (for example 5 seconds) depends mainly on the rapidity with which one bin 6 is expected to fill up in relation to the volume of grapes on the plants. The quicker the bin 6 fills the less time it takes to have an influence on the proportion of debris. The slower the bin 6 fills, the longer the time it takes to ensure that the average of the last n images processed is obtained from distinct levels of the crop and to avoid making an adjustment on the basis of an exceptionally incorrect proportion established from the surface of an invariant batch.

Steps 93, 94 and 95 are repeated until the end of the row of vines is reached (96). The end of the row of vines may be indicated by the driver by means of the console keyboard 86 or be automatically detected, for example, by detecting when the shakers stop. At the end of the vine row a return (97) is made to the waiting step 92 at the start of the next vine row unless the harvesting of the plot has finished. Otherwise the control system 16 is stopped (98).

The operation of the system 16 with respect to the system 1' is similar except for the difference that step 93 is omitted and that steps 94 and 95 calculate, respectively, the grape rate and its average over the last n images processed by the system 1'. The time lapse between two images involved in the average is e.g. one second.

This invention is, of course, susceptible to many variations and modifications apparent to the skilled person. In particular, although the invention has been described in relation to a particular example of a grape harvesting machine, it is applicable to any type of grape harvesting machine and, more generally, to any type of machine for harvesting fruit, berries and the like grown on trees or bushes planted in rows.

It will be understood that changes in the details, materials, steps and arrangements of parts which have been described and illustrated to explain the nature of the invention will occur to and may be made by those skilled in the art upon a reading of this disclosure within the principles and scope of the invention. The foregoing description illustrates the preferred embodiment of the invention; however, concepts, as based upon the description, may be employed in other embodiments without departing from the scope of the invention. Accordingly, the following claims are intended to protect the invention broadly as well as in the specific form shown.

Having thus described the invention, what is claimed is:

1. A method of harvesting agricultural crop material by means of a machine, comprising the steps of:

determining a proportion of at least one product in a mixture of products containing fruit and bodies foreign to the fruit by the following sub-steps:

taking shots in the near infrared by apparatus on said machine to obtain at least one initial image of the mixture to be examined;

thresholding comprising the allocation, to each pixel of the image, of one out of two extreme grey levels, corresponding to the initial grey level of the pixel in relation to a determined threshold; and calculation of said proportion comprising the recording, over at least one zone of the image produced by the thresholding, of the number of pixels of at least one extreme grey level to determine an area ratio between zones occupied respectively by crop material and foreign bodies in the image; and using the determined proportion to adapt at least one operating parameter of the machine which has an effect on said proportion.

2. The method of claim 1 wherein said threshold is derived automatically from the distribution of grey levels in said initial image.

3. The method of claim 1 further comprising, between the thresholding and recording steps, the steps of:

determining the outlines of patterns in the image produced by the thresholding substep with a first extreme grey level corresponding to the foreign bodies;

reducing in a peripheral and regular fashion, the area of said patterns by allocating a second extreme grey level to the pixels involved in order to obtain an intermediate image; and enlarging, in a peripheral and regular fashion, the area of the patterns of the first extreme grey level of the intermediate image, in order to reconstitute the image to be submitted to the recording substep, the peripheral expansion being performed by a same number of pixels as the peripheral reduction carried out to obtain the intermediate image.

4. A method of harvesting agricultural crop material by means of a machine, comprising the steps of:

determining a proportion of at least one product in a mixture of products containing fruit and bodies foreign to the fruit by the following sub-steps:

taking shots in the near infrared by apparatus on said machine to obtain at least one initial image of the mixture to be examined;

thresholding comprising the allocation, to each pixel of the image, of one out of two extreme grey levels, corresponding to the initial grey level of the pixel in relation to a determined threshold;

determining the outlines of patterns in the image produced by the thresholding substep with a first extreme grey level corresponding to the foreign bodies;

reducing in a peripheral and regular fashion, the area of said patterns by allocating a second extreme grey level to the pixels involved in order to obtain an intermediate image; and enlarging, in a peripheral and regular fashion, the area of the patterns of the first extreme grey level of the intermediate image, in order to reconstitute the image to be submitted to the recording substep, the peripheral expansion being performed by a same number of pixels as the peripheral reduction carried out to obtain the intermediate image; and recording, over at least one zone of the image produced by the thresholding, of the number of pixels of at least one extreme grey level to determine an area ratio between zones occupied respectively by crop material and foreign bodies in the image;

averaging area ratios calculated over a series of images to calculate a determined proportion; and using the determined proportion to adapt at least one operating parameter of the machine which has an effect on said proportion.

5. The method of claim 4 wherein the image subjected to the thresholding step is obtained from the difference between two separate frames of one image, or between two consecutive images, taken, respectively, with and without artificial lighting, at least by near infrared, of the zone under examination.

6. The method of claim 5 wherein, during the shot taking step, artificial back lighting is created from behind the zone under examination with respect to a means for making shots.

7. The method of claim 6 wherein said shot taking step comprises the steps of:

impulse-triggering the photosensitive charge coupled device elements of a camera; and lighting, at least in the near infrared, the zone under examination in at least every other exposure.

8. The method of claim 7 wherein said determined proportion is the proportion of foreign bodies in a batch of harvested crop material.

9. The method of claim 7 wherein said determined proportion is the proportion of crop material remaining on the field after the machine has passed.

10. The method of claim 7 wherein said operating parameter is the travel speed of the machine while harvesting.

11. The method of claim 7 wherein said crop material is berry-like fruit and the like growing on trees or bushes planted in rows, and the operating parameter is taken from the following:

frequency and/or amplitude of the movements of components of a shaker assembly;

linear speed of an intermediate conveyor receiving the harvested fruit;

parallelism of an approximately vertical median plane of the shaker assembly with respect to the trees or shrubs; and output of air from at least one means for pneumatic cleaning of the crop tipped into said temporary storage bin.

12. The method of claim 7 wherein said determining step determines the proportion of bodies foreign to the fruit in a batch of harvested fruit.

13. The method of claim 7 wherein said determining step determines the proportion of fruit remaining on the trees or bushes after the machine has passed.

14. In a machine for harvesting fruit growing on fruit trees or bushes planted in rows, having a high clearance chassis for travelling across fields; a shaker assembly mounted on said chassis to detach said fruit from said trees or bushes; and at least one conveyor for gathering the detached said fruit and guiding it into at least one temporary storage bin, the improvement comprising:

at least one device for determining a proportion of at least one product in a mixture of products, such as fruit and bodies foreign to the fruit, including:

apparatus mounted on said machine for taking shots in near infrared of said mixture of products to be examined;

means for processing the images to determine an area ratio between fruit and foreign bodies in at least one zone of an image obtained by said shot taking means; and means for controlling at least one operating parameter of the machine in relation to the proportion determined by said determining device.

15. The harvesting machine of claim 14 wherein said at least one operating parameter is taken from the following parameters:

the frequency and/or amplitude of the movements of the components which make up the shaker assembly;

the travel speed of the machine with respect to the trees or bushes;

the linear speed of an intermediate conveyor receiving the harvested fruit;

the parallelism of an approximately vertical median plane of the shaker assembly with respect to the trees or shrubs; and the output of air from at least one means for pneumatic cleaning of the crop tipped into said temporary storage bin.

16. The harvesting machine of claim 15 wherein said at least one determining device is associated with a bin for temporary storage of harvested fruit to determine the proportion of foreign bodies in a batch of harvested fruit in the bin.

17. The harvesting machine of claim 15 wherein said at least one determining device is installed at the rear of the machine with respect to its direction of travel in the course of harvesting, for determining the proportion of fruit remaining on trees or bushes.

18. The harvesting machine of claim 15 further comprising:

a first determining device associated with at least one temporary fruit storage bin for determining the proportion of foreign bodies in a batch of harvested fruit in the bin; and a second determining device installed at the rear of the machine in relation to its direction of travel for determining the proportion of fruit remaining on the trees or bushes.

19. The harvesting machine of claim 18 wherein said device for determining a proportion comprises:

means for taking shots in near infrared of said mixture of products to be examined; and means for processing the images to determine an area ratio between crop material and foreign bodies in at least one zone of an image obtained by said shot taking means (2, 2'), said processing means being operable to:

determine a proportion of at least one product in a mixture of products containing fruit and bodies foreign to the fruit; and use the determined proportion to adapt at least one operating parameter of the machine which has an effect on said proportion.

20. The harvesting machine of claim 19 wherein said determining device comprises at least one means for impulse lighting of the zone to be examined.

21. The harvesting machine of claim 20 further comprising at least one means for additional lighting placed opposite the shot taking means with respect to said mixture of products and directed towards the shot taking means.

22. The harvesting machine of claim 21 wherein the shot taking means comprises a camera provided with photo-sensitive charge coupled device elements associated with an electronic shutter to determine short periods of exposure of the photo-sensitive elements.

23. The harvesting machine of claim 22 wherein the camera is provided with a lens having a fixed focus and an automatic device for adjusting the sharpness of the image.

24. The harvesting machine of claim 23 wherein the camera is provided with a motorized zoom lens.

25. The harvesting machine of claim 18 further comprising:

means for controlling at least one operating parameter of the machine in relation to the proportion determined by said determining device.

26. The harvesting machine of claim 25 wherein said at least one operating parameter is taken from the following:

frequency and/or amplitude of the movements of components of the harvesting assembly;

travel speed of the machine; and linear speed of a conveyor receiving the harvested crop material.

27. The harvesting machine of claim 26 wherein said machine is a machine for harvesting berry-like fruit growing on fruit trees or bushes planted in rows, said chassis being a high clearance chassis for straddling said trees or bushes, and said harvesting assembly being a shaker assembly mounted on said chassis to detach berry-like fruit from said trees or bushes.

28. The harvesting machine of claim 25 wherein said at least one operating parameter is taken from the following:

parallelism of an approximately vertical median plane of the shaker assembly with respect to the trees or shrubs; and output of air from at least one means for pneumatic cleaning of the crop tipped into said temporary storage bin.

* * * * *